US010219869B2

(12) United States Patent
Seow

(10) Patent No.: US 10,219,869 B2
(45) Date of Patent: Mar. 5, 2019

(54) SURGICAL END EFFECTORS AND PULLEY ASSEMBLIES THEREOF

(71) Applicant: Covidien LP, Mansfield, MA (US)

(72) Inventor: Chi Min Seow, New Haven, CT (US)

(73) Assignee: Covidien LP, Mansfield, MA (US)

(*) Notice: Subject to any disclaimer, the term of this patent is extended or adjusted under 35 U.S.C. 154(b) by 225 days.

(21) Appl. No.: 15/116,339

(22) PCT Filed: Nov. 5, 2014

(86) PCT No.: PCT/US2014/064006
§ 371 (c)(1),
(2) Date: Aug. 3, 2016

(87) PCT Pub. No.: WO2015/122943
PCT Pub. Date: Aug. 20, 2015

(65) Prior Publication Data
US 2017/0014196 A1 Jan. 19, 2017

Related U.S. Application Data

(60) Provisional application No. 61/938,732, filed on Feb. 12, 2014, provisional application No. 61/938,728, filed on Feb. 12, 2014.

(51) Int. Cl.
A61B 34/30 (2016.01)
A61B 34/00 (2016.01)
(Continued)

(52) U.S. Cl.
CPC ............. *A61B 34/30* (2016.02); *A61B 34/35* (2016.02); *A61B 34/71* (2016.02); *F16H 19/005* (2013.01);
(Continued)

(58) Field of Classification Search
CPC ............ A61B 34/71; A61B 2017/2932; A61B 2017/2944; A61B 17/28; A61B 17/29
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CN 1547454 A 11/2004
(Continued)

OTHER PUBLICATIONS

Extended European Search Report corresponding to counterpart Int'l Appln. No. EP 14882554.0 dated Sep. 27, 2017.
(Continued)

Primary Examiner — Thomas McEvoy

(57) ABSTRACT

An end effector of a surgical tool includes a first jaw and a second jaw rotated by a driving pulley. A first driven pulley is attached to the first jaw and a second driven pulley is attached to the second jaw. A first end portion of a first cable is connected to a first radial side of the first driven pulley, a second end portion of the first cable is connected to a second radial side of the second driven pulley, and an intermediate portion of the first cable is connected to the driving pulley. A first end portion of a second cable is connected to a first radial side of the second driven pulley, a second end portion of the second cable is connected to a second radial side of the first driven pulley, and an intermediate portion of the second cable is connected to the driving pulley.

12 Claims, 7 Drawing Sheets

(51) Int. Cl.
  *F16H 19/00* (2006.01)
  *A61B 34/35* (2016.01)
  *F16H 19/08* (2006.01)
  *A61B 17/29* (2006.01)
  *A61B 17/3201* (2006.01)

(52) U.S. Cl.
  CPC .............. *F16H 19/08* (2013.01); *A61B 17/29* (2013.01); *A61B 17/3201* (2013.01); *A61B 2017/2932* (2013.01); *A61B 2017/2938* (2013.01); *A61B 2017/2944* (2013.01); *A61B 2034/715* (2016.02); *F16H 2019/085* (2013.01)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp |
| 6,032,849 A | 3/2000 | Mastri et al. |
| 6,045,560 A | 4/2000 | McKean et al. |
| 6,090,123 A | 7/2000 | Culp |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,969,385 B2 | 11/2005 | Moreyra |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |

(56) References Cited

U.S. PATENT DOCUMENTS

| | | |
|---|---|---|
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,074,859 B2 | 12/2011 | Kostrzewski |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,617,203 B2 | 12/2013 | Stefanchik et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0021859 A1 | 9/2001 | Kawai et al. |

(56) References Cited

U.S. PATENT DOCUMENTS

| | | |
|---|---|---|
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0074415 A1 | 4/2006 | Scott et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0108443 A1 | 5/2008 | Jinno et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0106145 A1 | 5/2011 | Jeong |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Lizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0238064 A1 | 9/2011 | Williams |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2011/0301637 A1 | 12/2011 | Kerr et al. |
| 2012/0000962 A1 | 1/2012 | Racenet et al. |
| 2012/0074199 A1 | 3/2012 | Olson et al. |
| 2012/0080475 A1 | 4/2012 | Smith et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0158013 A1 | 6/2012 | Stefanchik et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0110131 A1 | 5/2013 | Madhani et al. |
| 2013/0140835 A1* | 6/2013 | Stefanchik ............ A61B 17/29 294/106 |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |

(56) References Cited

U.S. PATENT DOCUMENTS

| | | | |
|---|---|---|---|
| 2015/0327850 | A1 | 11/2015 | Kostrzewski |
| 2015/0342601 | A1 | 12/2015 | Williams et al. |
| 2015/0342603 | A1 | 12/2015 | Zergiebel et al. |
| 2015/0374366 | A1 | 12/2015 | Zergiebel et al. |
| 2015/0374370 | A1 | 12/2015 | Zergiebel et al. |
| 2015/0374371 | A1 | 12/2015 | Richard et al. |
| 2015/0374372 | A1 | 12/2015 | Zergiebel et al. |
| 2015/0374449 | A1 | 12/2015 | Chowaniec et al. |
| 2015/0380187 | A1 | 12/2015 | Zergiebel et al. |
| 2016/0095585 | A1 | 4/2016 | Zergiebel et al. |
| 2016/0095596 | A1 | 4/2016 | Scirica et al. |
| 2016/0106406 | A1 | 4/2016 | Cabrera et al. |
| 2016/0113648 | A1 | 4/2016 | Zergiebel et al. |
| 2016/0113649 | A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 2005-125075 A | 5/2005 |
| KR | 10-0778387 | 11/2007 |
| KR | 10-2010-0001823 | 1/2010 |
| KR | 20120022521 A | 3/2012 |
| WO | 2009/051418 A2 | 4/2009 |
| WO | 2011/108840 A2 | 9/2011 |
| WO | 2011-115310 A1 | 9/2011 |
| WO | WO 2011-115310 | 9/2011 |
| WO | 2012/040984 A1 | 4/2012 |
| WO | 2014/012780 A1 | 1/2014 |
| WO | 2015-122943 A1 | 8/2015 |

OTHER PUBLICATIONS

International Search Report & Written Opinion corresponding to counterpart Int'l Appln. No. PCT/US2014/064006 dated Feb. 5, 2015.
International Search Report & Written Opinion corresponding to counterpart Int'l Appln. No. PCT/US2014/064009 dated Feb. 5, 2015.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appin. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2013101559718; 23 total pages.
International Search Report corresponding to PCT/US2014/061329 dated Jan. 28, 2015.
International Search Report for (PCT/US2014/064006) date of completion is Feb. 5, 2015 (3 pages).

* cited by examiner

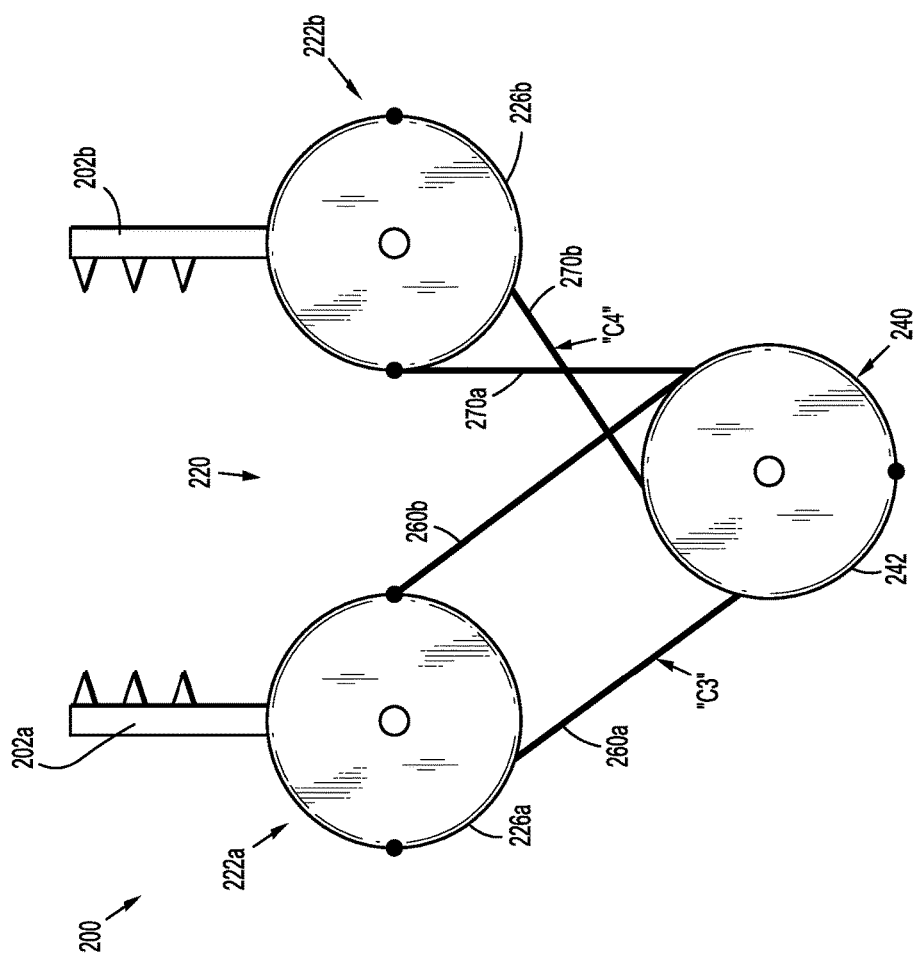

SURGICAL END EFFECTORS AND PULLEY ASSEMBLIES THEREOF

CROSS-REFERENCE TO RELATED APPLICATIONS

This application is a U.S. National Stage Application filed under 35 U.S.C. § 371(a) of International Patent Application Serial No. PCT/US2014/064006, filed Nov. 5, 2014, which claims the benefit of each of U.S. Provisional Patent Application Ser. No. 61/938,732, filed Feb. 12, 2014, and U.S. Provisional Patent Application Ser. No. 61/938,728, filed Feb. 12, 2014, the entire disclosure of each of which are incorporated by reference herein.

BACKGROUND

Robotic surgical systems have been used in minimally invasive medical procedures. Some robotic surgical systems included a console supporting a robot arm, and at least one end effector such as forceps or a grasping tool including jaws for capturing tissue therebetween. The at least one end effector was mounted to the robot arm. During a medical procedure, the end effector was inserted into a small incision (via a cannula) or a natural orifice of a patient to position the end effector at a work site within the body of the patient.

Cables extended from the console, through the robot arm, and connected to the end effector. In some instances, the cables were actuated by means of motors that were controlled by a processing system including a user interface for a surgeon or clinician to be able to control the robotic surgical system including the robot arm and/or the end effector. The cables connected to a pulley assembly that transferred torque to drive the actuation of the end effector.

In some instances, surgical procedures may require fine control of the end effector to grasp tissue for dissection and/or to spread tissue surfaces for deep tissue access. Accordingly, there is a need for surgical tools that are able to provide precisely controlled forces applied by jaws of an end effector of a robotic surgical system.

SUMMARY

Jaws at the end of surgical robotics tools, such as forceps or scissor cutting tools, may be driven by a pulley assembly including pulleys and cables. Methods for actuating an end effector at the end of the jaws are provided in some embodiments. Some methods may include rotating a driving pulley in an end effector of a surgical tool in a first direction about a first axis to open a first jaw and a second jaw, each being pivotable about a second axis.

The end effector may include a first driven pulley attached to the first jaw and a second driven pulley attached to the second jaw. The first and second driven pulleys may be rotatable about the second axis. Each driven pulley may include a first radial side and a second radial side. A first cable may have a first end portion, a second end portion, and an intermediate portion. The first end portion may be connected to the first radial side of the first driven pulley. The second end portion may be connected to the second radial side of the second driven pulley. The intermediate portion may be connected to the driving pulley.

The second cable may have a first end portion, a second end portion, and an intermediate portion. The first end portion may be connected to the first radial side of the second driven pulley. The second end portion may be connected to the second radial side of the first driven pulley. The intermediate portion may be connected to the driving pulley. Rotating the driving pulley in a second direction about the first axis may close the first and second jaws about the second axis.

The first and the second driven pulleys may be rotated via the first cable responsive to rotating the driving pulley in the first direction. The first and the second driven pulleys may be rotated via the second cable responsive to rotating the driving pulley in the second direction. The first cable may be tensioned and the second cable may be slackened during rotation of the driving pulley in the first direction. The second cable may be tensioned and the first cable may be slackened during rotation of the driving pulley in the second direction.

The intermediate portions of the first and second cables may be connected to a common point of the driving pulley. In some instances, the intermediate portions of the first and second cables may be crimped to the driving pulley.

The first end portion of the first cable may be parallel to the second end portion of the second cable. The first end portion of the second cable may be crossed with the second end portion of the first cable.

In some instances, a proximal end of the first jaw may be fixedly attached to a circumferential edge of the first drive pulley and a proximal end of the second jaw may be fixedly attached to a circumferential edge of the second drive pulley. A toothed portion may be created in the first and the second jaws.

The first axis may be spaced a lateral distance from the second axis. The first and second cables may be connected to the driving pulley at a location offset a radial distance from the second axis. The intermediate portions of the first and second cables may be looped through an anchor member on the driving pulley. A hook may be attached to a circumferential edge of the driving pulley.

In some instances, a method may include coupling a plurality of cable sections to a plurality of jaw pulleys with at least one cable section coupled to each of at least two radial sides of each jaw pulley. Each jaw pulley may be connected to a corresponding jaw. Each of the cable sections may be also be coupled to a driving pulley. The driving pulley may be rotated in a first and a second direction to rotate each of the jaw pulleys and at least one of open and close the jaws. Rotating the driving pulley in the first direction may create a tension in a different cable section coupled to each jaw pulley than rotating the driving pulley in the second direction.

Each of the cable sections may be separate cables or at least two of the cable sections may be part of a single continuous cable. A first segment of a first cable section of a continuous cable including at least two of the plurality of cable sections may be coupled to a radial side of a first jaw pulley. A second segment of the first cable section may be coupled to the driving pulley. A first segment of a second cable section of the continuous cable may be coupled to the driving pulley. A second segment of the second cable section may be coupled to a different radial side of the second jaw pulley.

A single segment of the continuous cable may be coupled to the driving pulley when the second segment of the first cable section coincides with the first segment of the second cable section. At least two segments of the continuous cable may be coupled to the driving pulley when the second segment of the first cable section does not coincide with the first segment of the second cable section.

In some instances a first segment of a first cable section of a continuous cable including at least two of the plurality of cable sections may be coupled to a radial side of a first jaw pulley. A second segment of the first cable section may be coupled to the driving pulley. A first segment of a second cable section of the continuous cable may be coupled to the driving pulley. A second segment of the second cable section may be coupled to a different radial side of the first jaw pulley. A single segment of the continuous cable may be coupled to the driving pulley when the second segment of the first cable section coincides with the first segment of the second cable section.

Further details and aspects of exemplary embodiments of the present disclosure are described in more detail below with reference to the appended figures.

As used herein, the terms parallel and perpendicular are understood to include relative configurations that are substantially parallel and substantially perpendicular, such as up to about + or −10 degrees from true parallel and true perpendicular.

BRIEF DESCRIPTION OF THE DRAWINGS

Embodiments of the present disclosure are described herein with reference to the accompanying drawings, wherein:

FIG. 6 is a schematic plan view, with parts separated, of a surgical end effector, according to another embodiment of the present disclosure, illustrating jaws and a pulley assembly thereof.

DETAILED DESCRIPTION

Figure 1A:
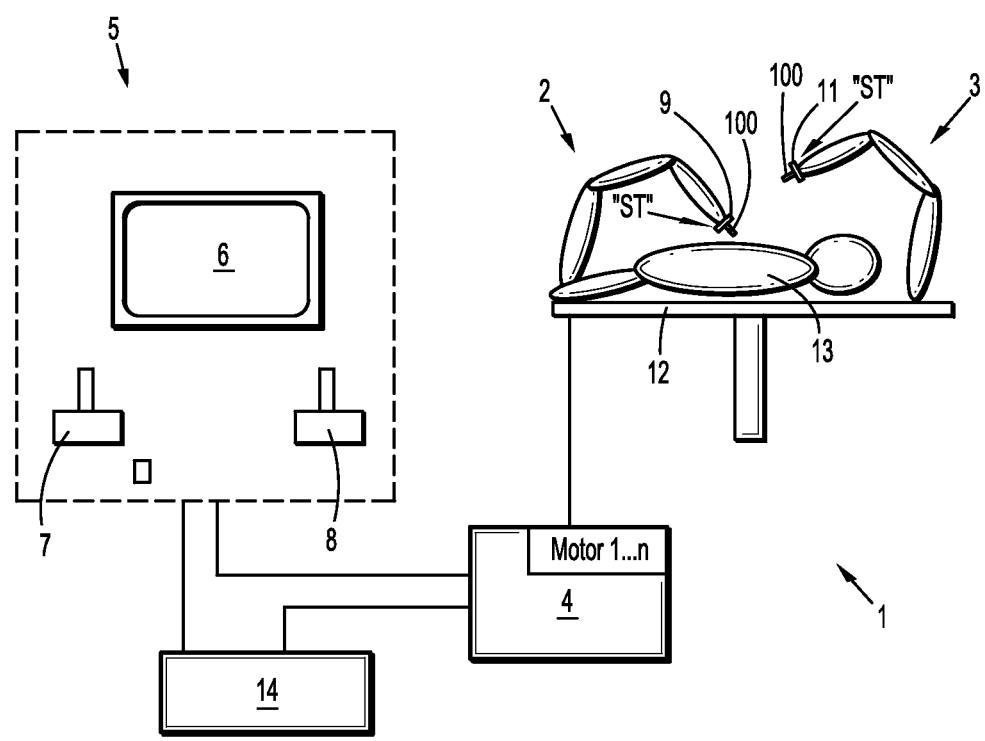
FIG. 1A is a schematic illustration of a medical work station and operating console in accordance with the present disclosure.

Embodiments of the presently disclosed surgical end effectors and methods of actuating the same are described in detail with reference to the drawings, in which like reference numerals designate identical or corresponding elements in each of the several views. As used herein the term "distal" refers to that portion of the jaws and/or pulley assembly that is closer to a surgical site, while the term "proximal" refers to that portion of the jaws and/or pulley assembly that is farther from the surgical site.

Figure 1B:
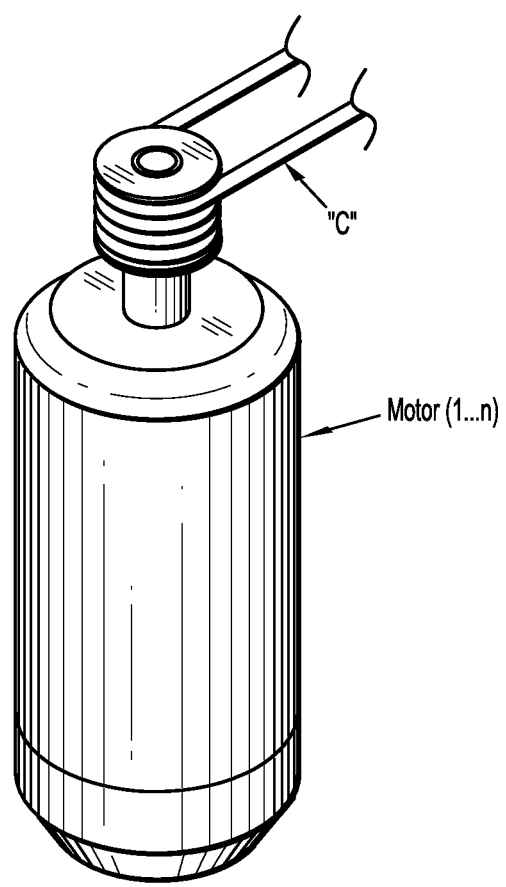
FIG. 1B is a schematic, perspective view of a motor of a control device of the medical work station of FIG. 1A, having a cable connected thereto.

Referring initially to FIGS. 1A and 1B, a medical work station is shown generally as work station 1 and may include one or more robot arms 2, 3; a control device 4; and an operating console 5 coupled with control device 4. Operating console 5 includes a display device 6, which is set up in particular to display three-dimensional images and/or video; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes an attaching device 9, 11, to which may be attached, for example, a surgical tool "ST" supporting an end effector 100, in accordance with any one of several embodiments disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, their attaching devices 9, 11 and thus the surgical tool (including end effector 100) execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of end effector 100. Medical work station 1 may also include one or more robot arms 2, 3, the additional robot arms likewise being connected to control device 4 and being telemanipulatable by means of operating console 5. A medical instrument or surgical tool (including an end effector 100) may also be attached to the additional robot arm. Medical work station 1 may include a database 14, in particular coupled to with control device 4, in which are stored for example pre-operative data from patient 13 and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (Motor 1 . . . n) with each motor configured to wind-up or let out a length of cable "C" (FIG. 1B) extending to end effector 100 of the surgical tool. The distal end of each cable "C" is wrapped around a driving pulley 140 of end effector 100 in the manner of a capstan to drive a rotation of driving pulley 140 as shown, for example, in FIG. 2. In use, as cables "C" are wound-up and let out, cables "C" effect operation and/or movement of each end effector 100 of the surgical tool via pulley assembly 120, as described in further detail herein below. It is contemplated that control device 4 coordinates the activation of the various motors (Motor 1 . . . n) to coordinate a winding-up or letting out a length of a respective cable "C" in order to coordinate an operation and/or movement of a respective end effector. Although FIG. 1B shows a single cable "C" that is wound up or let out by a single motor, in some instances two or more cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable configurations may be used in different embodiments.

Turning now to FIGS. 2-5, an end effector in accordance with an embodiment of the present disclosure is generally designated as 100. End effector 100 includes a first jaw 102a and a second jaw 102b. First and second jaws 102a, 102b are each rotatable or pivotable relative to one another. Each jaw 102a, 102b has a respective proximal end 104a, 104b and a respective distal end 106a, 106b. Each proximal end 104a, 104b is fixedly attached to first and second driven pulleys 122a, 122b, respectively, as described in further detail herein below. Each proximal end 104a, 104b of jaws 102a, 102b can be integrally connected to and/or monolithically formed with a circumferential edge of driven pulleys 122a, 122b, respectively. Each distal end 106a, 106b of jaws 102a, 102b defines a respective grip or toothed portion 108a, 108b in juxtaposed relation to one another. In use, as will be described in greater detail below, as driving pulley 140 is rotated in one of a clockwise and counter clockwise direction, jaws 102a, 102b will be caused to rotate, moving jaws 102a, 102b from a first, open configuration in which jaws 102a, 102b may receive tissue therebetween to a second, closed configuration in which jaws 102a, 102b may grasp tissue.

End effector 100 includes a pulley assembly 120 disposed therein for actuating jaws 102a, 102b of end effector 100. Pulley assembly 120 includes a first driven pulley 122a, a second driven pulley 122b, a driving pulley 140, a first cable "C1," and a second cable "C2." In FIG. 3A, cables C1 and C2 are each continuous cables that may have different cable sections, such as section S1 on cable C1 running from anchor member 180a on driven pulley 122a to anchor member 150 on driving pulley 140 and section S2 on cable C1 running from anchor member 150 to anchor member 180b on driven pulley 122b. Cable C2 may include cable sections S3 running from anchor member 182b on driven pulley 122a to anchor member 150 and section S4 running from anchor member 150 to anchor member 182a on driven pulley 122b.

Figure 3A:
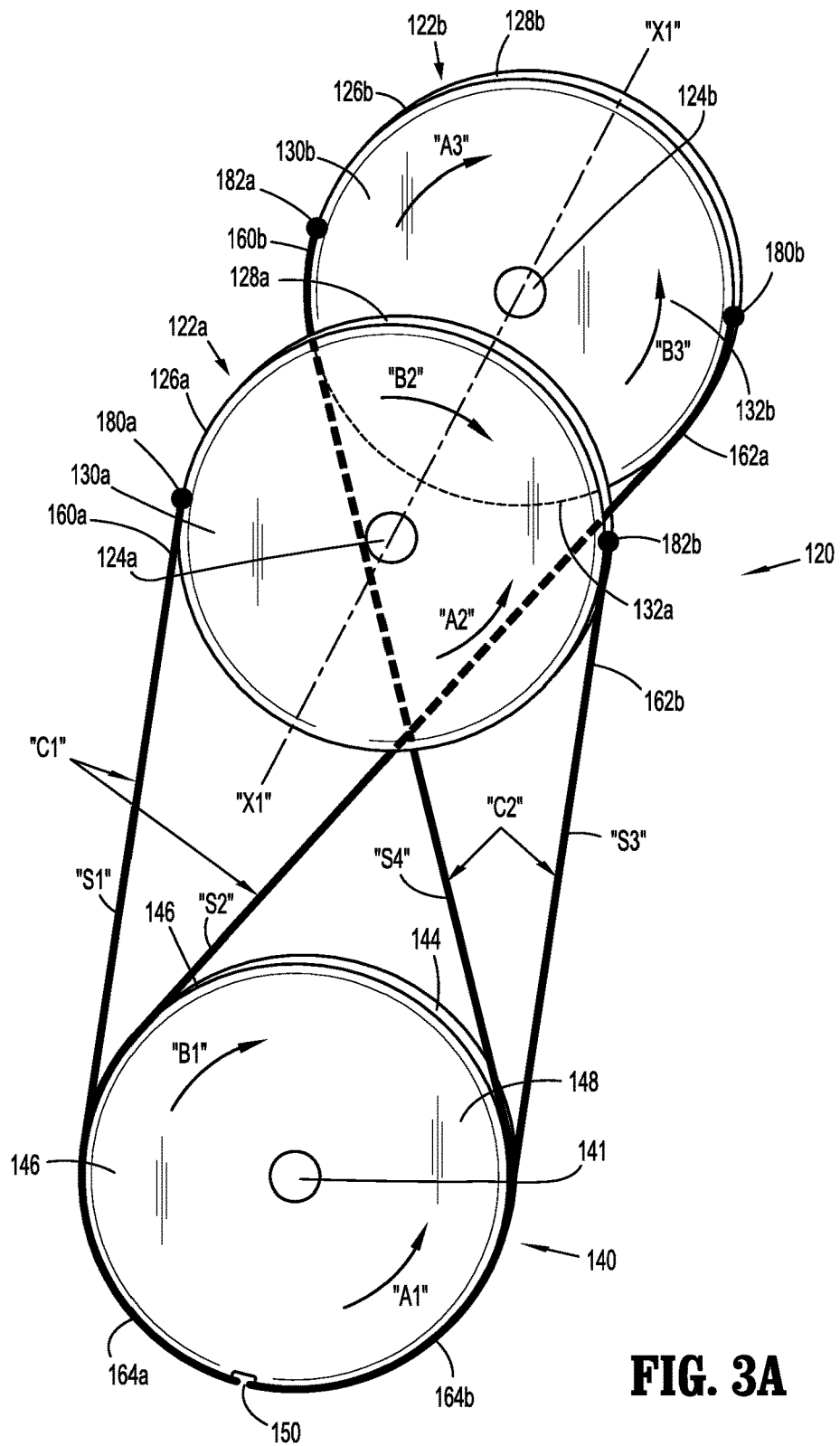
FIG. 3A is a perspective view of the pulley assembly of the end effector shown in FIG. 2.

In another embodiment that is a variation of that shown in FIG. 3A, cables C1 and C2 may also be continuous cables that may be attached to pulleys 122a, 122b, and 140 in a different manner. For example, continuous cable C1 may include a first section running from anchor member 180a on driven pulley 122a to anchor member 150 on driving pulley 140 (similar to section S1 in FIG. 3A) and a second section running from anchor member 150 to anchor member 182a on driven pulley 122b (similar to section S4 in FIG. 3A). Continuous cable C2 may include a first section running from anchor member 180b on driven pulley 122b to anchor member 150 (similar to section S2 in FIG. 3A) and a second section running from anchor member 150 to anchor member 182b on driven pulley 122a (similar to section S3 in FIG. 3A).

This configuration may result in a tensioning of a first section of cables C1 and C2 during a rotation of the driving pulley 140 in a first direction as well as a slacking of the other second section of cables C1 and C2. A tensioning of the second sections of cables C1 and C2 and a slacking of the first sections of cables C1 and C2 may occur when rotating the driving pulley 140 in the opposite direction. Other cable routings may be possible in different embodiments.

Figure 3B:
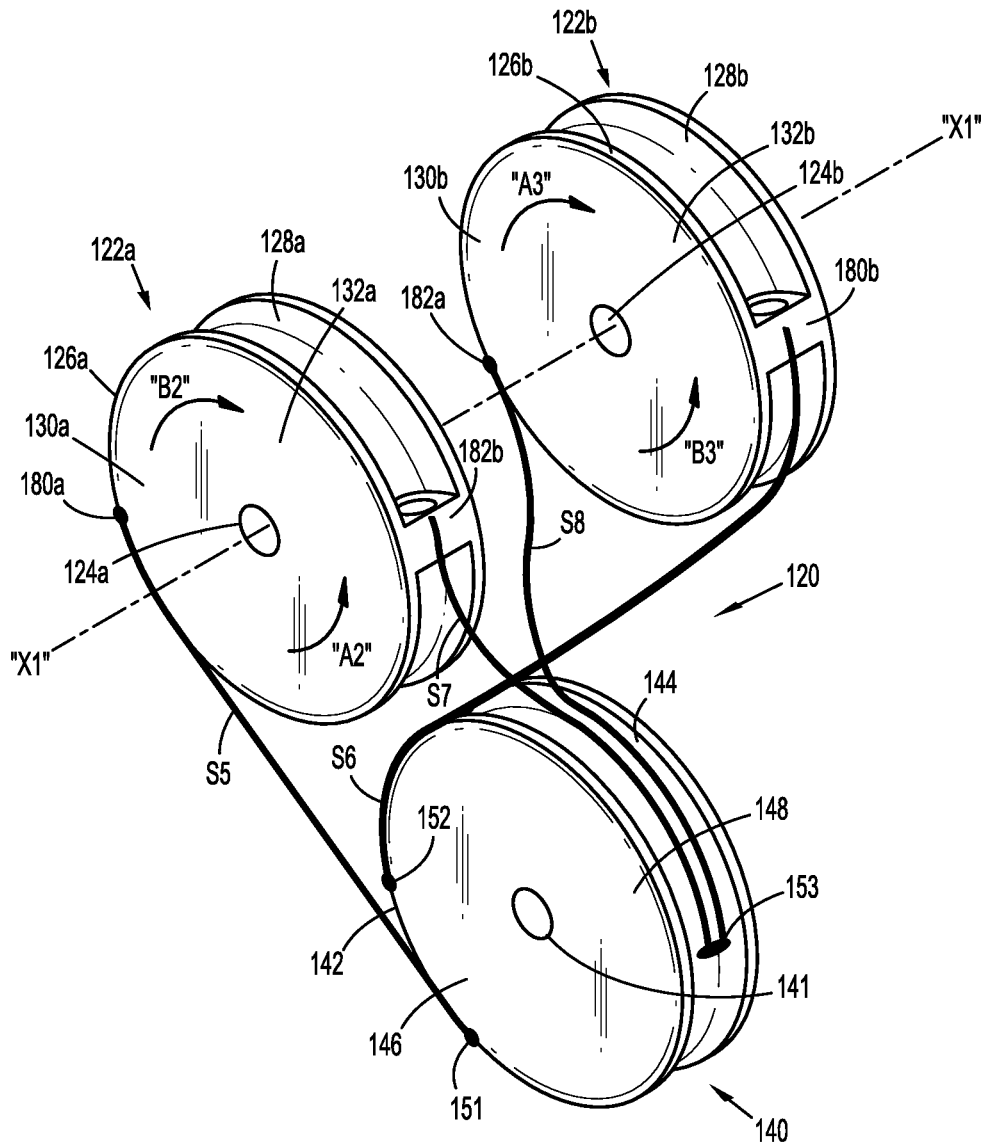
FIG. 3B is a perspective view of an alternate pulley assembly to that shown in FIG. 3A.

FIG. 3B shows another embodiment in which continuous cables C1 and C2 are replaced with four non-continuous sections of cable S5 to S8. In FIG. 3B, cable section S5 runs from anchor member 180a on driven pulley 122a to anchor member 151 on driving pulley 140. Cable section S6 runs from a different anchor member 152 on driving pulley 140 to anchor member 180b on driven pulley 122b. Cable section S7 runs from anchor member 182b on driven pulley 122a to anchor member 153 on driving pulley 140. Cable section S8 runs from anchor member 153 on driving pulley 140 to anchor member 182a on driven pulley 122b. Cables and/or cable sections may be connected to the same or different anchor members on the driving pulley 140 in different embodiments.

In embodiments, jaws 102a, 102b may be detachably engaged to driven pulleys 122a, 122b via a hinge, clips, buttons, adhesives, ferrule, snap-fit, threaded, and/or other engagement.

Each driven pulley 122a, 122b has a central opening 124a, 124b formed therein configured for disposal or receipt of a pivot pin (not shown) therein. Central openings 124a, 124b of each driven pulley 122a, 122b are in coaxial alignment with one another. A first axis "X1" extends through central openings 124a, 124b of first and second driven pulleys 122a, 122b. First and second driven pulleys 122a, 122b are disposed adjacent to one another and are rotatable relative to one another about first axis "X1." In some embodiments, driven pulleys 122a, 122b may be in abutting relation to one another or in spaced apart relation to one another, along first axis "X1." As mentioned above, first driven pulley 122a supports jaw 102a and second driven pulley 122b supports jaw 102b such that jaws 102a, 102b rotate with driven pulleys 122a, 122b about first axis "X1."

Driven pulleys 122a, 122b have a circular configuration and each define a circumferential edge 126a, 126b. Circumferential edges 126a, 126b each define an arcuate channel or groove 128a, 128b extending along a circumference of each driven pulley 122a, 122b. Channel or groove 128a, 128b is configured for receipt of one of cables "C1," "C2," as described in further detail herein below. In embodiments, driven pulleys 122a, 122b are variously configured, such as, for example, oval, oblong, tapered, arcuate, uniform, non-uniform and/or variable.

Figure 2:
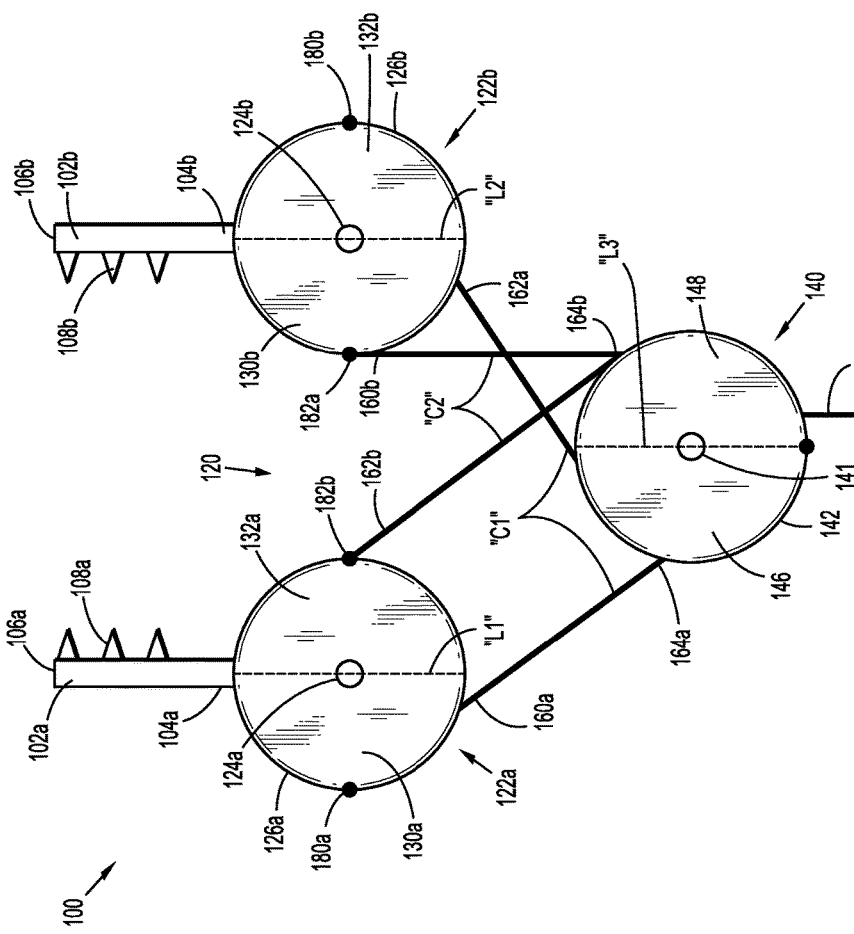
FIG. 2 is a schematic plan view, with parts separated, of a surgical end effector, according to an embodiment of the present disclosure, illustrating jaws and a pulley assembly thereof.

First driven pulley 122a includes a first radial side 130a and a second radial side 132a each defining a semicircular portion of first driven pulley 122a, as demarcated by dotted line "L1" in FIG. 2. First and second radial sides 130a, 132a each include one-half of circumferential edge 126a of first driven pulley 122a. Second driven pulley 122b includes a first radial side 130b and a second radial side 132b each defining a semicircular portion of second driven pulley 122b, as demarcated by dotted line "L2" in FIG. 2. First and second radial sides 130b, 132b of second driven pulley 122b include one-half of circumferential edge 126b of second driven pulley 122b.

Pulley assembly 120 further includes a driving pulley 140, similar to first and second driven pulleys 122a, 122b described herein above. Driving pulley 140 is spaced a lateral distance from first and second driven pulleys 122a, 122b. Cable "C," connected to motor (Motor 1 . . . n), may be wrapped at least once around driving pulley 140, in the manner of a capstan so as to not interfere with first and second cables "C1," "C2." Driving pulley 140 includes a central opening 141 formed therein. A second axis "X2" passes through central opening 141, is spaced a lateral distance from first axis "X1," and may run parallel to first axis "X1" in some instances. In other instances, the second axis "X2" may be offset from the first axis "X1" so that it runs at other non-parallel angles to the first axis "X1," such as perpendicular to the first axis.

Driving pulley 140 has a circular configuration and defines a circumferential edge 142. Circumferential edge 142 defines an arcuate channel or groove 144 extending along a circumference of driving pulley 140. Channel or groove 144 is configured for disposal of each of cables "C1," "C2." Driving pulley 140 includes a first radial side 146 and a second radial side 148 each defining a semicircular portion of driving pulley 140, as demarcated by dotted line "L3" in FIG. 2. First and second radial sides 146, 148 each include one-half of circumferential edge 142 of driving pulley 140.

Driving pulley 140 supports an anchor member 150 attached to a proximal-most portion of circumferential edge 142. Anchor member 150 secures both cables "C1," "C2" to drive pulley 140 such that, as driving pulley 140 is rotated, cables "C1," "C2" move therewith. In embodiments, anchor member 150 may be a hook onto which cables "C1," "C2" are attached. In other embodiments, anchor member 150 may be a crimp that secures cables "C1," "C2" to circumferential edge 142 of driving pulley 140.

In use, a rotation of driving pulley 140 about second axis "X2" via motor (Motor 1 . . . n) and cable "C" causes first and second driven pulleys 122a, 122b to rotate, via cables "C1," "C2," in opposing directions about first axis "X1" to open or close first and second jaws 102a, 102b, which are attached thereto.

Pulley assembly 120 may further includes a first cable "C1" and a second cable "C2." First cable "C1" and second cable "C2" each have a first end portion 160a, 160b, a second end portion 162a, 162b, and an intermediate portion or looped portion 164a, 164b. First and second cables "C1," "C2" are connected to first and second driven pulleys 122a, 122b and driving pulley 140 such that first end portion 160a of first cable "C1" and second end portion 162b of second cable "C2" are substantially parallel, and first end portion 160b of second cable "C2" and second end portion 162a of first cable "C1" cross, as shown in FIGS. 2-5.

First cable "C1" is secured by anchor member 150 of driving pulley 140 to a proximal-most portion of circumferential edge 142 of driving pulley 140 such that intermediate portion or looped portion 164a of first cable "C1" is fixedly engaged with a portion of circumferential edge 142 of driving pulley 140. Intermediate portion or looped portion 164a of first cable "C1" is connected to driving pulley 140 at a location off-set a radial distance from second axis "X2."

First end portion 160a of first cable "C1" is connected to a portion of circumferential edge 126a of first driven pulley 122a that is disposed on first radial side 130a of first driven pulley 122a. Second end portion 162a of first cable "C1" is connected to a portion of circumferential edge 126b of second driven pulley 122b that is disposed on second radial side 132b of second driven pulley 122b.

Figure 4:
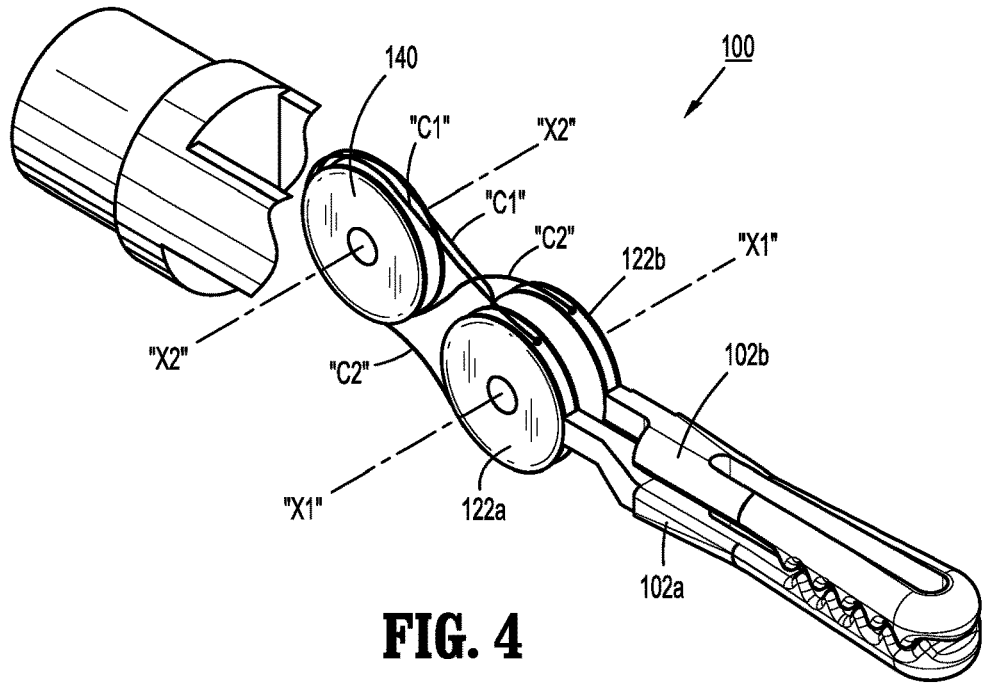
FIG. 4 is a perspective, cutaway view of the end effector shown in FIG. 2 with the jaws disposed in a closed configuration.
Figure 5:
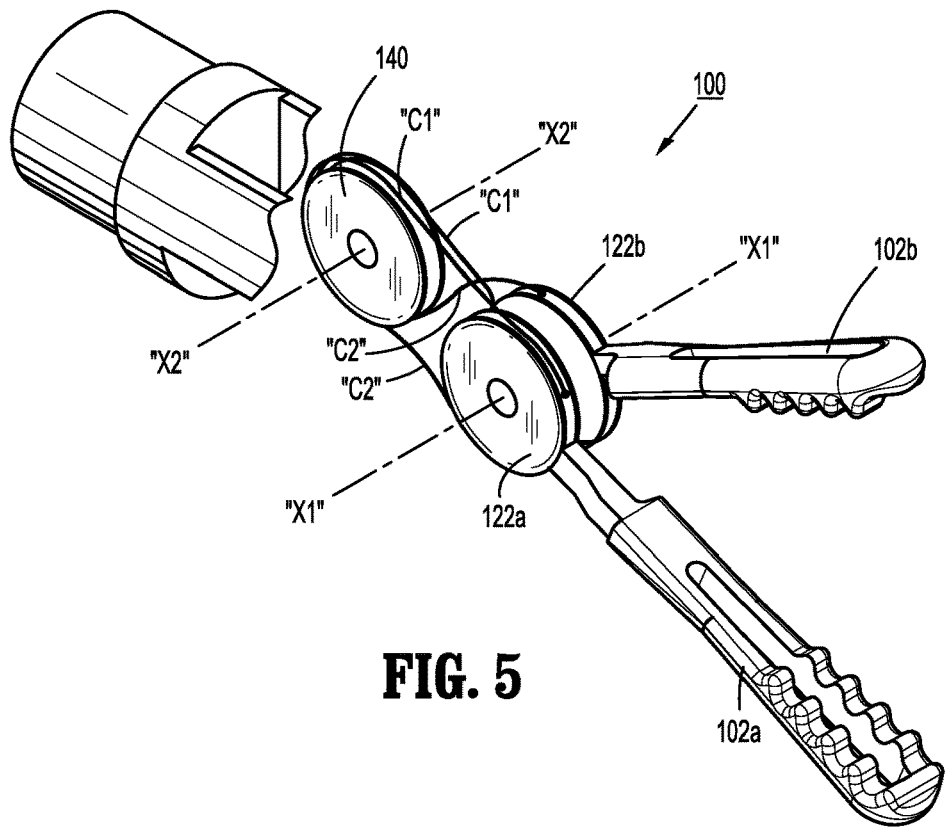
FIG. 5 is a perspective, cutaway view of the end effector shown in FIG. 2 with the jaws disposed in an open configuration.

First end portion 160a of first cable "C1" is connected to first radial side 130a of first driven pulley 122a via an anchor member 180a. Second end portion 162a of first cable "C1" is connected to second radial side 132b of second driven pulley 122b via an anchor member 180b. Anchor members 180a, 180b are similar to anchor member 150 described above. Each anchor member 150, 180a, 180b can be the same or may be different. In this way, intermediate portion or looped portion 164a of first cable "C1" is wrapped around only first radial side 146 of driving pulley 140, as shown in FIGS. 3A, 4, and 5.

Second cable "C2" is secured by anchor member 150 of driving pulley 140 to a proximal-most portion of circumferential edge 142 of driving pulley 140 such that intermediate portion or looped portion 164b of second cable "C2" is fixedly engaged with a portion of circumferential edge 142 of driving pulley 140. Intermediate portion or looped portion 164b of second cable "C2" is connected to driving pulley 140 at a location off-set a radial distance from second axis "X2." In this way, intermediate portions or looped portions 164a, 164b of first and second cables "C1," "C2" are connected to a common point of driving pulley 140.

First end portion 160b of second cable "C2" is connected to a portion of circumferential edge 126b of second driven pulley 122b that is disposed on first radial side 130b of second driven pulley 122b. Second end portion 162b of second cable "C2" is connected to a portion of circumferential edge 126a of first driven pulley 122a that is disposed on second radial side 132a of first driven pulley 122a.

First end portion 160b of second cable "C2" is connected to first radial side 130b of second driven pulley 122b via an anchor member 182a. Second end portion 162b of second cable "C2" is connected to second radial side 132a of first driven pulley 122a via an anchor member 182b. Anchor members 182a, 182b are similar to anchor member 150 described above. In this way, intermediate portion 164b of second cable "C2" is wrapped around only second radial side 148 of driving pulley 140, as shown in FIGS. 3-5.

In one embodiment, first cable "C1" includes two cables each having a first end connected to driving pulley 140 at a common point and a second end connected to first radial side 130a of first driven pulley 122a and second radial side 132b of second driven pulley 122b, respectively. Second cable "C2" may include two cables each having a first end connected to driving pulley 140 at a common point and a second end connected to first radial side 130b of second driven pulley 122b and second radial side 132a of first driven pulley 122a, respectively.

In operation, motor (Motor 1 . . . n) is energized to rotate and, in turn, drive a letting out or winding-up or a rotation of cable "C." As cable "C" is actuated, cable "C" drives the rotation of driving pulley 140 in one of a clockwise and counter-clockwise direction. A rotation of driving pulley 140 in a first direction, indicated by arrow "A1" shown in FIG. 3A, about second axis "X2," rotates first and second driven pulleys 122a, 122b via first cable "C1" about first axis "X1," in a direction indicated by arrows "A2," "A3" in FIG. 3A, respectively. During rotation of driving pulley 140 in the first direction, first cable "C1" is in a tensioned condition (shown in FIG. 3A) and second cable "C2" is in a slack condition. For example, as driving pulley 140 is rotated in the first direction, intermediate portion 164a of first cable "C1" rotates with driving pulley 140 about second axis "X2." As intermediate portion 164a of first cable "C1" rotates, first end portion 160a of first cable "C1" is pulled towards driving pulley 140 and, in turn, drives a rotation of first driven pulley 122a in the same direction as the direction in which driving pulley 140 is rotating. Second end portion 162a of first cable "C1" is also pulled towards driving pulley 140 and, in turn, drives a rotation of second driven pulley 122b in an opposite direction as the direction in which driving pulley 140 is rotating. In this way, jaws 102a, 102b, which are attached to driven pulleys 122a, 122b, respectively, are opened about first axis "X1."

A rotation of driving pulley 140 in a second direction, indicated by arrow "B1" shown in FIG. 3A, rotates first and second driven pulleys 122a, 122b via second cable "C2" about first axis "X1," in a direction indicated by arrows "B2," "B3" in FIG. 3A, respectively. During rotation of driving pulley 140 in the second direction, first cable "C1" is in a slack condition and second cable "C2" is in a tensioned condition (shown in FIG. 3A). For example, as driving pulley 140 is rotated in the second direction, intermediate portion 164b of second cable "C2" rotates with driving pulley 140 about second axis "X2." As intermediate portion 164b of second cable "C2" rotates, first end portion 160b of second cable "C2" is pulled towards driving pulley 140 and, in turn, drives a rotation of second driven pulley 122b in an opposite direction as the direction in which driving pulley 140 is rotating. Second end portion 162b of second cable "C2" is also pulled towards driving pulley 140 and, in turn, drives a rotation of first driven pulley 122a in the same direction in which driving pulley 140 is rotating. In this way, jaws 102a, 102b, which are attached to driven pulleys 122a, 122b, respectively, are closed about first axis "X1."

In one embodiment, as shown in FIG. 6, an end effector 200, similar to end effector 100 described above with regard to FIGS. 2-5, is shown. End effector 200 includes a first jaw 202a and a second jaw 202b, similar to jaws 102a, 102b described above. First and second jaws 202a, 202b are each pivotable about a first axis (not shown). End effector 200 further includes a pulley assembly 220, similar to pulley assembly 120 described above. Pulley assembly 220 is disposed within end effector 200 for actuating jaws 202a, 202b of end effector 200.

Pulley assembly 220 includes a first driven pulley 222a, a second driven pulley 222b, a driving pulley 240, a first cable "C3," and a second cable "C4," similar to first driven pulley 122a, second driven pulley 122b, driving pulley 140, first cable "C1," and second cable "C2," respectively, described above. In accordance with the present embodiment, first cable "C3" and second cable "C4" may be in the form of a cable loop or the like.

First driven pulley 222a supports jaw 202a and second driven pulley 222b supports jaw 202b such that jaws 202a, 202b rotate with driven pulleys 222a, 222b about the first axis. Driven pulleys 222a, 222b have a circular configuration and each define a circumferential edge 226a, 226b configured for disposal or receipt of first and second cables "C3," "C4," respectively.

Driving pulley 240 is spaced a lateral distance from first and second driven pulleys 222a, 222b. Cable "C," connected to motor (Motor 1 . . . n), may be wrapped at least once around driving pulley 240, in the manner of a capstan so as to not interfere with first and second cables "C3," "C4." Driving pulley 240 has a circular configuration and defines a circumferential edge 242 configured for disposal or receipt of each of cables "C3," "C4."

First cable "C3" is looped or wrapped about circumferential edge 242 of driving pulley 240 and circumferential edge 226a of first driven pulley 222a such that, a first half 260a and a second half 260b of cable "C3" are in parallel relation to one another. Second cable "C4" is looped or wrapped about circumferential edge 242 of driving pulley 240 and circumferential edge 226b of second driven pulley 222b such that, a first half 270a and a second half 270b of cable "C4" are in a criss-cross or figure-eight pattern.

In use, a rotation of driving pulley 240 via motor (Motor 1 . . . n) and cable "C" causes first and second driven pulleys 222a, 222b to rotate, via cables "C3," "C4," in opposing directions to open or close first and second jaws 202a, 202b, which are attached thereto.

It will be understood that various modifications may be made to the embodiments disclosed herein. For example, while the driven pulleys disclosed herein have been shown and described as being connected to the proximal ends of the jaws, it is contemplated and within the scope of the present disclosure, for the driven pulleys to be operatively connected with the distal portion of the jaws. Therefore, the above description should not be construed as limiting, but merely as exemplifications of various embodiments. Those skilled in the art will envision other modifications within the scope and spirit of the claims appended thereto.

What is claimed is:

1. A method of actuating an end effector, comprising:
    rotating a driving pulley in an end effector of a surgical tool in a first direction about a first axis to open a first jaw and a second jaw each being pivotable about a second axis, the end effector including:
    a first driven pulley attached to the first jaw and a second driven pulley attached to the second jaw, the first and second driven pulleys being rotatable about the second axis, each driven pulley including a first radial side and a second radial side;
    a first cable having a first end portion, a second end portion, and an intermediate portion, the first end portion connected to the first radial side of the first driven pulley, the second end portion connected to the second radial side of the second driven pulley, and the intermediate portion connected to the driving pulley; and
    a second cable having a first end portion, a second end portion, and an intermediate portion, the first end portion connected to the first radial side of the second driven pulley, the second end portion connected to the second radial side of the first driven pulley, and the intermediate portion connected to the driving pulley; and
    rotating the driving pulley in a second direction about the first axis to close the first and second jaws about the second axis.

2. The method as recited in claim 1, further comprising:
    rotating the first and the second driven pulleys via the first cable responsive to rotating the driving pulley in the first direction; and
    rotating the first and the second driven pulleys via the second cable responsive to rotating the driving pulley in the second direction.

3. The method as recited in claim 2, further comprising:
    tensioning the first cable and slacking the second cable during rotation of the driving pulley in the first direction and the second cable is in a slack condition; and
    tensioning the second cable and slacking the first cable during rotation of the driving pulley in the second direction.

4. The method as recited in claim 1, further comprising connecting the intermediate portions of the first and second cables to a common point of the driving pulley.

5. The method as recited in claim 1, further comprising crimping the intermediate portions of the first and second cables to the driving pulley.

6. The method as recited in claim 1, further comprising:
    positioning the first end portion of the first cable parallel to the second end portion of the second cable; and
    crossing the first end portion of the second cable and the second end portion of the first cable.

7. The method as recited in claim 1, further comprising fixedly attaching a proximal end of the first jaw to a circumferential edge of the first drive pulley and a proximal end of the second jaw to a circumferential edge of the second drive pulley.

8. The method as recited in claim 1, further comprising creating a toothed portion in the first and the second jaws.

9. The method as recited in claim 1, further comprising spacing the first axis a lateral distance from the second axis.

10. The method as recited in claim 1, further comprising connecting the first and second cables to the driving pulley at a location offset a radial distance from the second axis.

11. The method as recited in claim 1, further comprising looping the intermediate portions of the first and second cables through an anchor member on the driving pulley.

12. The method as recited in claim 1, further comprising attaching a hook to a circumferential edge of the driving pulley.

* * * * *